US00PP29056P2

(12) United States Plant Patent
DeVries

(10) Patent No.: US PP29,056 P2
(45) Date of Patent: Mar. 6, 2018

(54) ***ILEX* PLANT NAMED 'GG11'**

(50) Latin Name: *Ilex verticillata*
Varietal Denomination: GG11

(71) Applicant: Leendert D. DeVries, Arcata, CA (US)

(72) Inventor: Leendert D. DeVries, Arcata, CA (US)

(73) Assignee: Trinity Valley Vineyards LLC, Arcata, CA (US)

( * ) Notice: Subject to any disclaimer, the term of this patent is extended or adjusted under 35 U.S.C. 154(b) by 0 days.

(21) Appl. No.: 15/330,692

(22) Filed: Oct. 27, 2016

(51) Int. Cl.
*A01H 5/00* (2006.01)

(52) U.S. Cl.
USPC ..... Plt./247

(58) Field of Classification Search
USPC ..... Plt./247
See application file for complete search history.

*Primary Examiner* — Annette H Para
(74) *Attorney, Agent, or Firm* — Samuel R. McCoy Jr.

(57) ABSTRACT

A new and distinct *Ilex verticillata* cultivar named 'GG11' which is characterized by vigorous growth, a large amount of strong, upright main stems with numerous lateral branches, and very early fruiting with medium-sized vibrant orange berries along the entire length of the lateral branches. The claimed plant propagates successfully by softwood stem cuttings and has proven to be uniform and stable in the resulting generations.

2 Drawing Sheets

Latin name of the genus and species: The Latin name of the genus and species of the novel variety disclosed herein is *Ilex verticillata.*

Variety denomination: The inventive variety of *Ilex verticillata* disclosed herein has been given the variety denomination 'GG11'.

BACKGROUND OF THE INVENTION

The present invention relates to a new and distinct variety of *Ilex verticillata*, which has been given the denomination, 'GG11'. *Ilex verticillata*, known commonly as winterberry, is a deciduous perennial that is widely cultivated for its ornate berries born along the lateral branches. The berries persist for many months through fall and winter, making it an ideal plant for ornamental landscaping in its hardiness range and also for the cut flower industry. Its market class is PLT/247.

Parentage: The new cultivar 'GG11' is a seedling selection resulting from the open pollination of *Ilex verticillata* 'Magical Times' (unpatented in the United States), the seed parent, and an undesignated male *Ilex verticillata* plant, the pollen parent. In 2005, seeds were harvested from 'Magical Times' which resulted in approximately 2000 seedlings. In March of 2006, the seedlings were transplanted into a field in Willow Creek, Calif. and grown to a mature size. From 2006 to 2011, these plants were evaluated for commercial production, based on criteria such as growth habit and fruiting habit. In the fall of 2009, one plant was observed which exhibited an upright growth habit with a large number of very strong main stems, each with a high density of medium-sized, vibrant orange berries along the entire length of the lateral branches. The new plant was isolated and grown to a mature size to confirm the distinctness and stability of the characteristics initially observed. After further evaluation and confirmation of the desirable traits, the claimed plant was finally selected for commercialization in September of 2011 and given the breeder denomination, 'GG11'.

Asexual Reproduction: In the summer of 2010, 'GG11' was first asexually reproduced in Willow Creek, Calif. by way of softwood stem cuttings taken from one year old growth. The claimed plant was found to asexually reproduce in uniform and stable manner and three successive cycles of vegetative propagation have proven to be true to type.

SUMMARY OF THE INVENTION

The following characteristics have been repeatedly observed and represent the distinguishing characteristics of the new *Ilex verticillata* cultivar 'GG11'. These traits, in combination, distinguish 'GG11' as a new and distinct cultivar.

1. 'GG11' exhibits excellent plant vigor and a fast rate of growth; and
2. 'GG11' exhibits a large quantity of very strong and upright main stems; and
3. 'GG11' exhibits short lateral branches; and
4. 'GG11' exhibits very early fruiting, setting berries in mid-August in Willow Creek, Calif.; and
5. 'GG11' exhibits a large quantity of berries born along the entire length of the lateral branches, including the distal most portion of the lateral branches usually devoid of berries in the species; and
6. 'GG11' exhibits medium-sized, vibrant orange berries.

BOTANICAL DESCRIPTION OF THE PLANT

Figure 1:
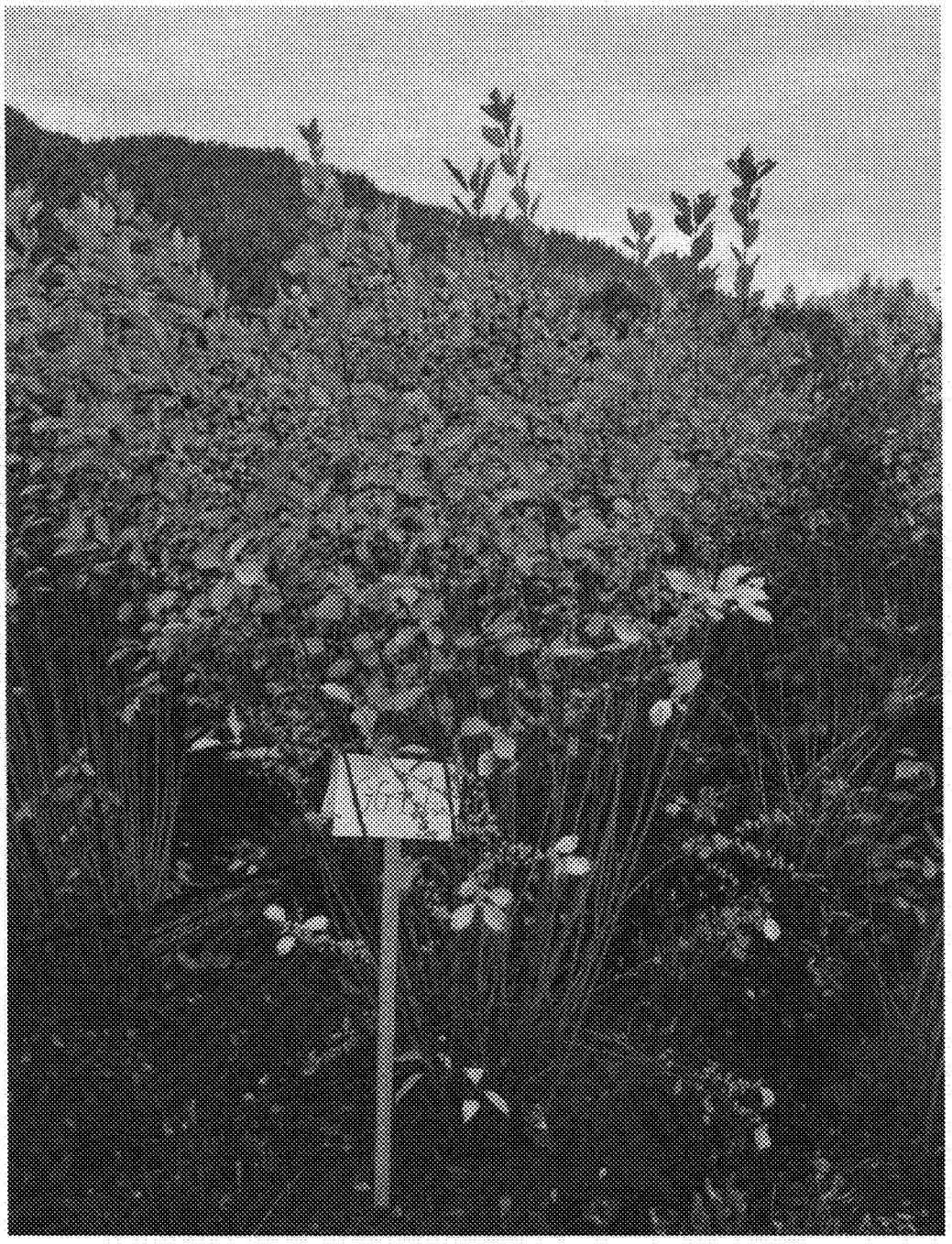
FIG. 1 illustrates, as nearly true as it is reasonably possible to make the same in color photographs of this type, an exemplary 2 year old field-grown 'GG11' plant in Willow Creek, Calif.
Figure 2:
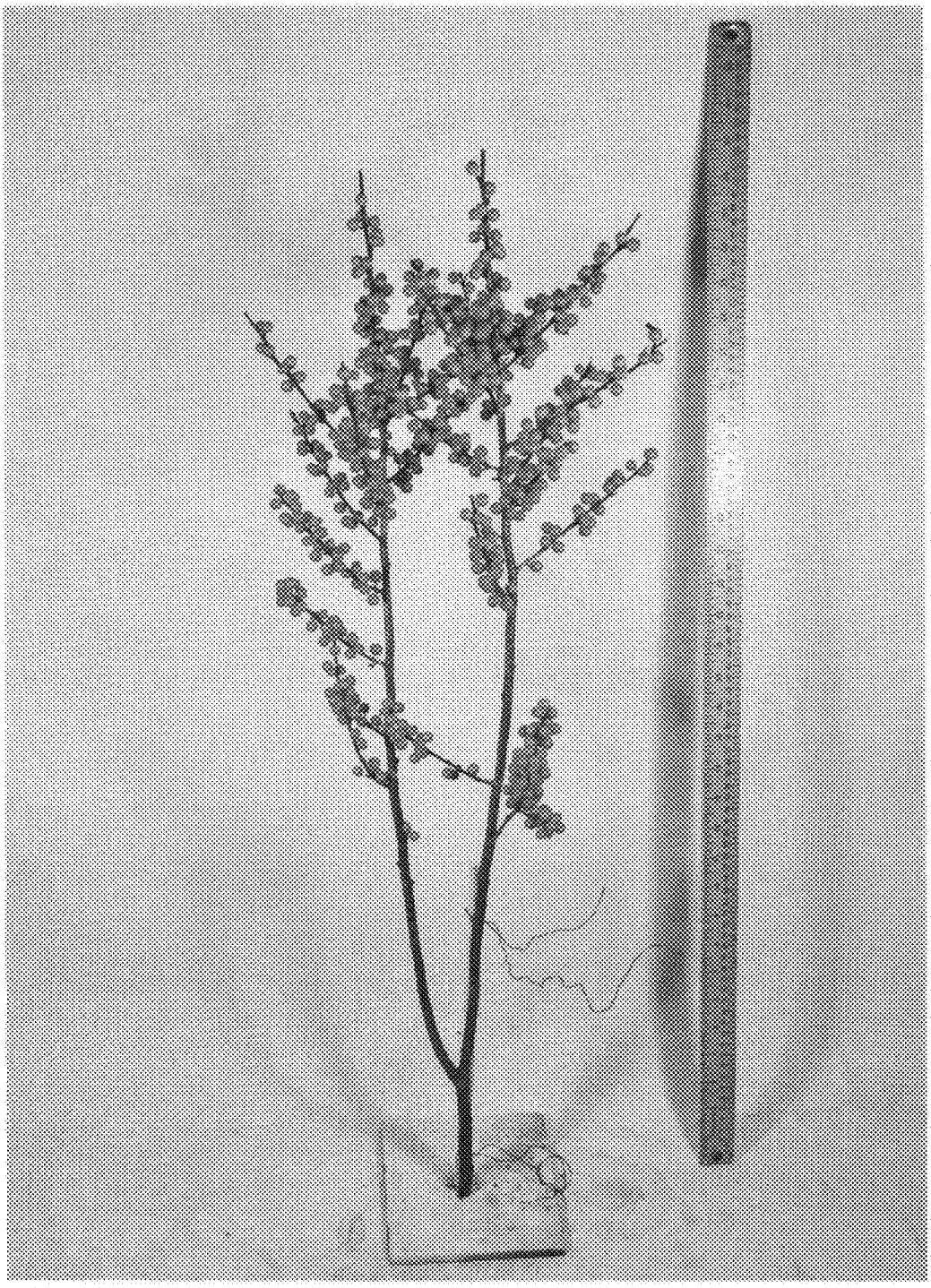
FIG. 2 illustrates, as nearly true as it is reasonably possible to make the same in color photographs of this type, a cut stem with fruit, harvested from an exemplary two year old field grown 'GG11' plant in Willow Creek, Calif.

The following is a detailed botanical description of a new and distinct variety of a *Ilex verticillata* known as 'GG11'. Plant observations were made on field grown plants produced in Willow Creek, Calif. Unless indicated otherwise, the descriptions disclosed herein are based upon observations made of a mature 'GG11' plant, transplanted into a loamy clay field in May of 2015 as an 8 month old rooted cutting grown in a 4 inch nursery pot. The plant was grown using conventional production techniques for this species. The plant was provided overhead irrigation for two months after transplant and thereafter received regular drip irrigation. Fertilizer was regularly applied using a fertigation technique, and the plant was occasionally treated for mites when required. In February of 2016, the plant was pruned to 7 cm above soil level and have since been allowed to grow without further pruning. Observation data was recorded in the October of 2016.

Those skilled in the art will appreciate that certain characteristics will vary with older or, conversely, younger plants. 'GG11' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 1986 edition except where common terms of color are used.

A botanical description of 'GG11' and comparisons with the presumed parents are provided below.

General plant description:

*Plant habit*.—Deciduous perennial shrub with an upright growth habit and excellent plant vigor. *Ilex verticillata* is a dioecious plant and 'GG11' is a female plant of the species.

*Height*.—Approximately 107 cm.

*Width*.—Approximately 46 cm.

*Environmental tolerances*.—Hardy in US Hardiness Zones 3 through 9; high tolerance to wind and rain.

*Pest and disease susceptibility or resistance*.—Plants have not been observed to be susceptible or resistant to pathogens and pests common to *Ilex verticillata*.

*Propagation*.—Propagation is accomplished using softwood stem cuttings.

*Time to develop roots*.—Approximately 21 days, in a propagation house with bottom heat and an average ambient temperature of 25 degrees Celsius.

*Crop time*.—Approximately 5 weeks are needed to produce a fully rooted cutting; cuttings rooted into 4 inch nursery containers during the summer are subsequently transplanted into a production field in Willow Creek, Calif., in the following spring. From these plants, fruit bearing stems can be harvested in early fall of the following year.

Root system:

*Description*.—A network of larger primary roots and fine, fibrous lateral roots.

*Rooting habit*.—Freely branching, dense, and evenly distributed throughout the soil profile.

*Color, primary roots*.—Greyed-orange, RHS 165A.

*Color, lateral roots*.—Greyed-yellow, RHS 161D.

Stems:

*Branching habit*.—Free, basally branching habit; numerous upright main stems, each producing numerous lateral branches. Main stems are typically unbranched, yet occasionally branched.

*Main stems*.—Quantity — 27. Attitude — Erect; near vertical. Cross section — Circular. Diameter — Up to 12 mm, at the base of the most mature stems. Length — Longest stem is 107 cm long. Internode length — Varying from 5 to 30 mm. Color — Nearest to Greyed-brown, RHS 199D, yet slightly lighter. Texture — Smooth, glabrous. Strength — Very strong.

*Lateral branches*.—Quantity — Lower lateral branches senescing with age; 8 to 10 lateral branches per main stem which are present on the upper half of main stems. Stem angle to main axis — In between 60 and 80 degrees. Cross-section — Circular. Diameter — 3 mm at the base. Length — Longest lateral branch is 15.25 cm long. Internode length — Varying from 5 to 20 mm. Color, juvenile — Yellow-green, RHS 152A. Color, mature — Greyed-orange, RHS 165A. Texture — Smooth, glabrous; lenticels present. Lenticels are elliptical; approximately 1.0 mm long and 0.75 mm wide; color is greyed-brown, RHS 199D. Stem strength — Strong.

Foliage:

*Arrangement*.—Alternate.

*Attachment*.—Petiolate.

*Division*.—Simple.

*Shape*.—Ovate.

*Length*.—76 mm.

*Width*.—47 mm.

*Apex*.—Acuminate.

*Base*.—Cuneate.

*Margin*.—Serrulate.

*Aspect*.—Nearly flat.

*Texture and pubescence, adaxial surface*.—Slightly rugose and glabrous.

*Texture and pubescence, abaxial surface*.—Smooth to slightly rugose and glabrous with the exception of a few small hairs on the midrib.

*Color*.—Juvenile foliage, adaxial surface — Yellow-green, RHS 147A. Juvenile foliage, abaxial surface — Yellow-green, RHS 147B. Mature foliage, adaxial surface — Yellow-green, RHS 147A. Mature foliage, abaxial surface — Yellow-green, RHS 147B.

*Venation*.—Pattern — Pinnate. Vein color, adaxial surface — The midrib is yellow-green, nearest to RHS 144B; all other veins are yellow-green, RHS 147A. Vein color, abaxial surface — The midrib and all secondary veins are yellow-green, nearest to RHS 145B.

*Petiole*.—Length — 15 mm. Diameter — 2.0 mm. Color, adaxial surface — Yellow-green, RHS 144B, and suffused with greyed-orange, RHS 165B. Color, abaxial surface — Yellow-green, RHS 144B, and suffused with greyed-orange, RHS 165B. Texture, adaxial and abaxial surfaces — Smooth; glabrous.

Inflorescence:

*Type*.—Solitary female flowers occurring at the leaf axils, with 3 to 6 flowers at each axil.

Flower bud:

*Shape*.—Round to short ovoid.

*Dimensions*.—Approximately 2.5 mm long and 2.5 mm in diameter.

*Color, upper and lower surfaces*.—Nearest to yellow-green, RHS 145D.

Flower:

*General description*.—Single rotate flowers with a shallow cup shape; flowers are female.

*Natural flowering season*.—May through early June in Willow Creek, Calif.

*Quantity*.—3 to 6 flowers per axil, with approximately 6 to 9 flowers on shorter proximal lateral branches and 28 to 30 on longer distal lateral branches.

*Lastingness*.—At greater than 25 degrees Celsius, petals drop away in approximately 5 days; at 15 degrees Celsius, petals drop away in approximately 8 days.

*Persistence*.—Not persistent.

*Fragrance*.—Not fragrant.

*Attitude*.—Flowers held upright and slightly outward.

*Dimensions*.—Corolla is 7.5 mm in diameter and 2.5 to 2.75 mm deep.

*Peduncle*.—Dimensions — 1.5 mm long and 1 mm in diameter. Color — Yellow-green, RHS 144B. Texture — Smooth; glabrous. Strength — Medium.

*Calyx*.—Shape — Sepals fused at the base forming a cup, with 6 to 7 rotate sepal lobes. Diameter — 2.5 to 3.0 mm, measured from apex of one sepal lobe to the apex of an opposing sepal lobe. Depth — Approximately 2.5 mm deep. Quantity of sepal lobes — 6 to 7 sepal lobes; typically 6. Apex, sepal lobes — Sepal lobes acute. Base — Fused. Margin — Entire; ciliate. Texture, inner and outer surfaces — Smooth and glabrous. Color when opening, inner surface — Nearest to yellow-green, RHS 144C. Color when opening, outer surface — Yellow-green, RHS 144C. Color when fully open, inner surface — Yellow-green, RHS 144B. Color when fully open, outer surface — Yellow-green, RHS 144C.

*Petals*.—Quantity of petals — 6 to 7 petals, fused at the base; typically with 6 petals. Arrangement — Single rotate whorl. Petal lobe apex — Obtuse. Petal lobe margin — Entire; slightly undulated. Texture, inner and outer surfaces — Smooth; glabrous. Luster, inner and outer surfaces — Matte to very slightly glossy. Color when opening, inner surface — White, RHS 155C. Color when opening, outer surface — White, RHS 155C. Color when fully open, dorsal surface — Nearest to white, RHS 155C; petals are slightly translucent. Color when fully open, ventral surface — Nearest to white, RHS 155C; petals are slightly translucent. Petal color fading to — Not fading.

Reproductive organs:

*Androecium*.—Stamens — Quantity — 6 to 7 sterile stamens. Position — Inserted; free. Attachment — One stamen attached at the base of each petal. Overall length — Approximately 1.25 mm long. Filament — Dimensions — 0.5 mm long and approximately 0.25 mm in diameter. Color — Green-white, RHS 157D. Anthers — Attachment — Basifixed. Shape — Nearly globose, with a longitudinal split. Dimensions — 0.75 mm long and 0.5 mm wide. Color — Green-white, RHS 157A. Pollen — None.

*Gynoecium*.—Pistils — Quantity — One; inferior to the corolla. Overall dimensions — Approximately 1.0 to 1.25 mm tall and 1.5 to 1.75 mm in diameter at the stigma. Stigma — Shape — Globular. Dimensions — 1.5 to 1.75 mm in diameter, and 0.5 mm tall. Color — Yellow-green, approximating to a combination of RHS 144C and 144D. Style — Shape — Relatively broad, and truncated. Dimensions — 0.5 to 0.75 mm tall and 1.5 mm in diameter. Color — Yellow-green, RHS 144B. Ovary — Position — Superior. Dimensions — 0.5 to 0.75 mm tall and 1.5 mm in diameter. Color — Yellow-green, RHS 144B.

Fruit and seed:

*Fruit*.—Type — Simple, indehiscent berry. Time to maturity — Very early to fruit, maturing usually near the middle of August in Willow Creek, Calif. Shape — Globose. Quantity — 3 to 6 berries per axil, with approximately 9 berries on shorter proximal lateral branches and 28 to 30 on longer distal lateral branches. Dimensions — Approximately 8 mm in diameter, and 8 mm tall. Texture, pubescence and luster — Smooth, glabrous and glossy. Color, mature fruit — Orange-red, approximating to a combination of RHS 33A and 34A.

*Seed*.—Quantity — Usually 4 per berry. Shape — Oblong, three-sided, with an ovate to deltoid outline. Dimensions — 4 to 4.5 mm long and 1.5 mm in diameter. Color — Greyed-orange, RHS 165D. Texture — Slightly rough.

COMPARISON WITH THE PARENT PLANTS

Plants of the new cultivar 'GG11' differ from the seed parent, *Ilex verticillata* 'Magical Times', by the characteristics described in Chart 1. The pollen parent is unknown and therefore no comparison is available.

CHART 1

| Characteristic | 'GG11' | 'Magical Times' |
|---|---|---|
| Timing of fruit maturation, | Typically in mid-August; three weeks earlier than 'Magical Times' and the earliest marketable variety known to the inventor. | Typically in the second week of September; three weeks later than 'GG11'. |
| Occurrence of berries on lateral branches. | Berries present along the entire length of lateral branches. | Berries only present on approximately 60 percent of lateral branches; distalmost portion devoid of berries. |
| Productivity; number of harvestable main stems. | 27, resulting in more harvestable cut stems. | 10 to 12, resulting in much fewer harvestable cut stems. |

COMPARISON WITH THE MOST SIMILAR *ILEX VERTICILLATA* CULTIVAR KNOWN TO THE INVENTOR

Plants of the new cultivar 'GG11' are most similar to the cultivar, *Ilex verticillata* 'Golden Verboom' (not patented in the United States). A comparison of 'GG11' with *Ilex* 'Golden Verboom' is described in Chart 2.

CHART 2

| Characteristic | 'GG11' | 'Golden Verboom' |
|---|---|---|
| Timing of fruit maturation. | Typically in mid-August; four weeks earlier than 'Golden Verboom' and the earliest marketable variety known to the inventor. | Typically in the third week of September; four weeks later than 'GG11'. |
| Occurrence of berries on lateral branches. | Berries present along the entire length of lateral branches. | Berries only present on approximately 50 percent of lateral branches; distalmost portion devoid of berries. |

CHART 2-continued

| Characteristic | 'GG11' | 'Golden Verboom' |
|---|---|---|
| Productivity; number of harvestable main stems. | 27, resulting in more harvestable cut stems. | 8 to 12, resulting in much fewer harvestable cut stems. |

That which is claimed is:

1. A new and distinct variety of *Ilex verticillata* plant named 'GG11', substantially as described and illustrated herein.

* * * * *